(12) United States Patent
Nakada

(10) Patent No.: US 7,375,811 B2
(45) Date of Patent: May 20, 2008

(54) FATIGUE-DEGREE EVALUATION DEVICE

(75) Inventor: Masato Nakada, Schaumburg, IL (US)

(73) Assignee: Tanita Corporation, Tokyo (JP)

( * ) Notice: Subject to any disclaimer, the term of this patent is extended or adjusted under 35 U.S.C. 154(b) by 479 days.

(21) Appl. No.: 11/209,616

(22) Filed: Aug. 24, 2005

(65) Prior Publication Data

US 2007/0055449 A1    Mar. 8, 2007

(51) Int. Cl.
*G01N 21/64* (2006.01)
(52) U.S. Cl. .................... 356/417; 250/458.1; 436/172
(58) Field of Classification Search ................. 356/417
See application file for complete search history.

(56) References Cited

U.S. PATENT DOCUMENTS 6,596,258 B1 *   7/2003   Ballesteros Garcia et al. ... 424/9.3

2001/0031913 A1*  10/2001  Ito et al. .................... 600/300

FOREIGN PATENT DOCUMENTS

| JP | 2003-098177 | * | 4/2003 |
| JP | 2004-117084 | | 4/2004 |

\* cited by examiner

*Primary Examiner*—F. L. Evans
(74) *Attorney, Agent, or Firm*—McDermott Will & Emery LLP

(57) ABSTRACT

A fatigue-degree evaluation device is provided for easily evaluating a degree of fatigue of a living body. Embodiments include a device wherein fluorescent light generated via a liquid excreted from a body is measured; the temperature of the liquid excreted from the body is measured; a pH is calculated based on the fluorescent light and the temperature of the liquid excreted from the body; and a fatigue degree is evaluated based on this pH.

23 Claims, 7 Drawing Sheets

| SALIVA pH | . . . 7 . . . 6 . . . 5 . . . 4 . . . 3 . . . 2 . . . |
|---|---|
| FATIGUE DEGREE | . . . 0 . . . 1 . . . 2 . . . 3 . . . 4 . . . 5 . . . |

FATIGUE-DEGREE EVALUATION DEVICE

FIELD OF THE INVENTION

The present invention relates to a fatigue evaluation device for measuring a degree of fatigue (hereinafter "fatigue degree") of a living body based on a pH obtained by measuring fluorescent light generated through a liquid excreted (exhausted) from the body.

DESCRIPTION OF THE RELATED ART

To quantitatively obtain a fatigue degree, conventional techniques extract and directly measure a substance produced in a body along with fatigue, such as lactic acid, using a chromatographic instrument. Also, a pH value of a secondary product, such as saliva, which results from the presence of a fatigue related substance in the circulatory process of the body and is excreted (exhausted) therefrom, has been measured using an electrochemical measuring instrument. Such techniques are disclosed in Japanese Unexamined Patent Application Publication No. 2004-117084.

However, in the chromatographic instrument described above, there have been problems in that a large physical burden is applied to an examinee because of the need for collection of the fatigue related substance, such as lactic acid, from the body. Moreover, personal acquisition of such a device is difficult for an examinee because the instrument is large and expensive. Also, in this electrochemical measuring instrument, an electrode, which comes in direct contact with the secondary product, degrades quickly and needs to be replaced frequently.

SUMMARY OF THE INVENTION

Accordingly, the present invention has been made in view of the conventional problems mentioned above and it is an object thereof to provide a fatigue degree evaluation device capable of simply evaluating a degree of fatigue produced in a body.

In order to achieve the object mentioned above, a fatigue-degree evaluation device according to the present invention includes fluorescent-light measuring means for measuring the fluorescent light of a liquid excreted from a body; pH calculating means for calculating a pH based on the fluorescent light, measured by the fluorescent-light measuring means, of the liquid excreted from the body; and fatigue-degree evaluating means for evaluating a fatigue degree based on the pH calculated by the pH calculating means.

The fatigue-degree evaluation device according to the present invention can further include fluorescent-light measurement determination processing means for determining whether the fluorescent-light measuring means has normally measured the fluorescent light of the liquid excreted from the body. When the fluorescent light of the liquid excreted from the body is determined to have been normally measured, the result is incorporated as fluorescent light data, and when the fluorescent light of the liquid excreted from the body is determined to have been not normally measured, the result is communicated to the user.

The fatigue-degree evaluation device according to the present invention can further include temperature measuring means for measuring the temperature of the liquid excreted from the body. The pH calculating means calculates the pH based on the fluorescent light, measured by the fluorescent-light measuring means, of the liquid excreted from the body and the temperature, measured by the temperature measuring means, of the liquid excreted from the body.

The fatigue-degree evaluation device according to the present invention can further include temperature measurement determination processing means for determining whether the temperature measuring means has normally measured the temperature of the liquid excreted from the body. When the temperature of the liquid excreted from the body is determined to have been normally measured, the result is incorporated as temperature data, and when the temperature of the liquid excreted from the body is determined to have been not normally measured, the result is communicated to the user.

The fatigue-degree evaluation device according to the present invention can further include clock means for measuring an elapsed time of measurement; and elapsed-time measurement determination processing means for determining whether the elapsed time of measurement measured by the clock means exceeds a predetermined time. When the elapsed time exceeds the predetermined time as a result of determination, the result is communicated to the user, and when the elapsed time does not exceed the predetermined time, the fluorescent-light measuring means is controlled to measure the fluorescent light.

In the fatigue-degree evaluation device according to the present invention, the fluorescent-light measuring means can include a radiating unit for radiating reference light based on an AC constant current, a fluorescent-light reaction unit for retaining the liquid excreted from the body thereon and for fluorescent-reacting based on the reference light radiated by the radiating unit, and a detection unit for detecting the fluorescent light generated based on the fluorescent reaction of the fluorescent-light reaction unit.

In the fatigue-degree evaluation device according to the present invention, the fluorescent-light measuring means, the pH calculating means, and the fatigue-degree evaluating means can include a bar-like body, comprising a bar having an extremity with a bifurcated end and a connection part, and having a lead-in path arranged at the extremity for leading the liquid excreted from the body to the fluorescent-light reaction unit, and a holding body made to be easily held by a hand at the connection part, so as to form a casing.

In the fatigue-degree evaluation device according to the present invention, the holding body can be formed of front and back surfaces, having a width and a height, and top and bottom surfaces, having a width and a depth; the holding body extending in the longitudinal direction of the bar-like body, the width of the front and back surfaces being larger than their height, the depth of the top and bottom surfaces being smaller than the height of the front and back surfaces, and a recess being provided in the front and back surfaces.

In certain embodiments of the fatigue-degree evaluation device according to the present invention, the height of the front and back surfaces is not less than 20 mm.

In certain embodiments of the fatigue-degree evaluation device according to the present invention, the bar-like body does not exceed 50 mm in length.

In the fatigue-degree evaluation device according to the present invention, the fluorescent-light reaction unit can include a liquid-adsorption member and a fluorescent screen arranged in contact with the liquid-adsorption member and having a fluorescent substance adhered thereon, and the radiating unit can include an emission unit for radiating reference light and a first optical filter for diffusing the reference light from the emission unit to the fluorescent screen, and the detection unit can include a second optical filter for condensing the fluorescent light generated in the fluorescent screen and an optical receiver for receiving the fluorescent light from the second optical filter.

In the fatigue-degree evaluation device according to the present invention, the emission unit, the first optical filter, the second optical filter, and the optical receiver can constitute a packaged optical system unit.

In the fatigue-degree evaluation device according to the present invention, the liquid excreted from the body can be saliva.

In the fatigue-degree evaluation device according to the present invention, the liquid excreted from the body can be urine.

The components of the fatigue-degree evaluation device according to the present invention do not easily degrade during detection of the liquid excreted from the body, and inexpensive components can be used, since the measurement is based on a fluorescent reaction. Therefore, the device can be used without frequent component replacements, thereby simplifying evaluation of the fatigue degree of the body.

In certain embodiments of the fatigue-degree evaluation device according to the present invention, in accordance with whether the measurement of the fluorescent light of the liquid excreted from the body is normal or not, a fluorescent-light measurement determination processing means takes the measurement as fluorescent data or informs the user that the measurement is not normal, respectively, so the device is user-friendly, enabling the fatigue degree of a body to be evaluated more simply.

In certain embodiments of the fatigue-degree evaluation device according to the present invention, the pH is calculated by factoring in the temperature of the liquid excreted from the body, so error due to temperature is reduced, enabling the fatigue degree of the body to be evaluated simply and precisely.

In certain embodiments of the fatigue-degree evaluation device according to the present invention, in accordance with whether the measurement of the temperature of the liquid excreted from the body is normal or not, a temperature measurement determination processing means takes the measurement as temperature data or informs the user that the measurement is not normal, respectively, so the device is user-friendly, enabling the fatigue degree of a body to be evaluated more simply.

In certain embodiments of the fatigue-degree evaluation device according to the present invention, in accordance with whether the measurement of the elapsed time of measurement exceeds a predetermined time or not, an elapsed time measurement determination processing means informs the user that the elapsed time of measurement exceeds the predetermined time or controls the fluorescent-light measuring means to measure the fluorescent light, respectively, so sufficient measurement data can be obtained, enabling the fatigue degree of the body to be evaluated simply and precisely.

In certain embodiments of the fatigue-degree evaluation device according to the present invention, a fluorescent-light measuring means detects the fluorescent light generated in the fluorescent-light reaction unit at the detection unit based on reference light radiated from a radiating unit, so that fluorescent data can be positively obtained, enabling the fatigue degree of the body to be evaluated simply and securely.

In certain embodiments of the fatigue-degree evaluation device according to the present invention, a casing is composed of a bar-like body having a lead-in path and a holding body made to be easily held by hand, so that the measurement can be precisely and simply performed, enabling the fatigue degree of the body to be evaluated more simply.

In certain embodiments of the fatigue-degree evaluation device according to the present invention, the holding body extends in the longitudinal direction of the bar-like body, the width of the front and back surfaces is larger than their height, the depth of the top and bottom surfaces is smaller than the height of the front and back surfaces, and a recess is provided in the front and back surfaces, so that the device can be easily and always supported, enabling the fatigue degree of the body to be evaluated simply and precisely.

In certain embodiments of the fatigue-degree evaluation device according to the present invention, the height of the front and back surfaces of the holding body is not less than 20 mm, so that the holding body is prevented from being inserted into a user's mouth, enabling the fatigue degree of the body to be evaluated simply and precisely.

In certain embodiments of the fatigue-degree evaluation device according to the present invention, the bar-like body does not exceed 50 mm in length, so that the bar-like body is prevented from being excessively inserted into a user's mouth, enabling the fatigue degree of the body to be evaluated simply and precisely.

In certain embodiments of the fatigue-degree evaluation device according to the present invention, reference light generated in an emission unit is diffused by a first optical filter so as to impinge on a fluorescent screen arranged in contact with a liquid-adsorption member, and the fluorescent light generated in the fluorescent screen is condensed in a second optical filter so as to be received by an optical receiver, so that the measurement is positively determined, enabling the fatigue degree of the body to be evaluated simply and reliably.

Since the emission unit, the first optical filter, the second optical filter, and the optical receiver are packaged into an optical system unit, handling is facilitated, enabling the fatigue degree of the body to be evaluated more simply.

In the fatigue-degree evaluation device according to the present invention, the liquid excreted from the body can be saliva or urine, so the sample for the measurement can be simply obtained, enabling the fatigue degree of the body to be evaluated more simply.

BRIEF DESCRIPTION OF THE DRAWINGS

Reference is made to the attached drawings, wherein elements having the same reference numeral designations represented like elements throughout, and wherein:

FIGS. 1A to 1C are external views of a fatigue-degree evaluation device according to an embodiment of the present invention, wherein FIG. 1A is a view of an end to be taken in a mouth, FIG. 1B is a view of the upper surface of a holding body 21*b*, and FIG. 1C is a view of the front of the holding body 21*b*;

DESCRIPTION OF THE INVENTION

Figure 1A:
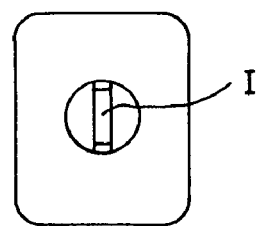

A fatigue degree evaluation device according to the present invention is composed of fluorescent-light measuring means, fluorescent-light measurement determination processing means, temperature measuring means, temperature measurement determination processing means, clock means, elapsed-time determination processing means, pH calculating means, and fatigue degree evaluating means.

The fluorescent-light measuring means measures fluorescent light of a liquid, such as saliva and urine, excreted (exhausted) from a body.

The fluorescent-light measurement determination processing means determines whether the fluorescent-light measuring means is normally (i.e., properly) measuring the fluorescent-light of the liquid excreted from the body or not. If the determined result is that the fluorescent-light of the liquid excreted from the body is normally measured, the result is incorporated as fluorescent data, and if the fluorescent light is not normally measured, the result is communicated to the user.

The temperature measuring means measures the temperature of the liquid, such as saliva and urine, excreted from the body.

The temperature measurement determination processing means determines whether the temperature measuring means is normally measuring the temperature of the liquid excreted from the body or not. If the determined result is that the temperature of the liquid excreted from the body is normally measured, the result is incorporated as temperature data, and if the temperature is not normally measured, the result is communicated to the user.

The clock means measures elapsed time for the measurement.

The elapsed-time determination processing means determines whether the elapsed time measured by the clock means exceeds a predetermined time (one minute, preferably) or not. If the determined result is that the elapsed time exceeds the predetermined time, the result is communicated to the user, and if the elapsed time does not exceed the predetermined time, the fluorescent-light measuring means is controlled to measure fluorescent light.

The pH calculating means calculates the pH of the liquid excreted from the body based on the fluorescent light measured by the fluorescent-light measuring means, and on the temperature of the liquid measured by the temperature measuring means. More specifically, the fluorescent light varies in accordance with the pH of the liquid excreted from the body and in accordance with the temperature of the liquid excreted from the body. The relationship between these factors is as follows:

$$pH = p \times \arg[\{(a \times T + b) \times \text{Vhum} + c\} / \{(d \times T + e) \times \text{Vref}\} + \delta] + q,$$

where pH: pH of the liquid excreted from the body,

T: the temperature of the liquid excreted from the body,

Vhum: the fluorescent light (voltage) of the liquid excreted from the body,

Vref: the reference light (voltage), with which the liquid excreted from the body is irradiated, and a, b, c, d, e, p, q, δ: constant.

By substituting the fluorescent light, measured by the fluorescent-light measuring means, generated via the liquid excreted from the body, and the temperature of the liquid measured by the temperature measuring means into this equation, the pH of the liquid excreted from the body is calculated.

The fatigue degree evaluating means evaluates the fatigue degree based on the pH calculated by the pH calculating means. More specifically, the pH of the liquid excreted from the body varies in accordance with the fatigue degree, so the relationship between the pH and the fatigue degree (which is obtained in advance) can be used to evaluate the fatigue degree corresponding to the pH calculated by the pH calculating means.

In the fatigue degree evaluation device constructed as described above, the fluorescent light generated via the liquid excreted from the body is measured by the fluorescent-light measuring means; the temperature of the liquid is measured by the temperature measuring means; the pH is calculated by the pH calculating means based on the fluorescent light and the temperature of the liquid excreted from the body; and the fatigue degree is evaluated by the fatigue degree evaluating means based on this pH. According to this device, components do not easily degrade during detection of the liquid excreted from the body; and inexpensive components can be used because the measurement is based on a fluorescent reaction, so the inventive device can be used by an individual without frequent component replacements, thereby simplifying evaluation of the fatigue degree of the body.

Also, in the inventive fatigue degree evaluation device, in accordance with whether the measurement of the fluorescent light and the temperature of the liquid excreted from the body is normal or not, the fluorescent-light measurement determination processing means and the temperature measurement determination processing means take the measurement as data or inform the user that the measurement is not normal, respectively, so that the inventive device is precise and user-friendly.

Also, in the inventive fatigue degree evaluation device, when the elapsed time of the measurement exceeds a predetermined time (one minute, preferably), the elapsed-time determination processing means informs a user of the result, and when it does not exceed the predetermined time, it controls the device to perform the measurement again, enabling sufficient and precise measurement data to be obtained.

In the inventive fatigue degree evaluation device described above, the pH calculating means calculates the pH in consideration of the temperature of the liquid excreted from the body; alternatively, the pH calculating means can calculate the pH based on the fluorescent light, measured by the fluorescent-light measuring means, generated via the liquid excreted from the body neglecting the temperature of the liquid. More specifically, the fluorescent light varies in accordance with the pH of the liquid excreted from the body according to the following relationship:

$$pH = p \times \arg[(\gamma \times \text{Vhum} + \epsilon) / (\phi \times \text{Vref} + \delta)] + q,$$

where pH: the pH of the liquid excreted from the body,

Vhum: the fluorescent light (voltage) of the liquid excreted from the body,

Vref: the reference light (voltage), with which the liquid excreted from the body is irradiated, and p, q, γ, ε, φ, δ: constant.

By substituting the fluorescent light, measured by the fluorescent-light measuring means, generated via the liquid excreted from the body into this equation, the pH of the liquid excreted from the body can also be calculated.

The fatigue degree evaluation device described above will be described in more detail by exemplifying a fatigue degree evaluation device according to an embodiment of the present invention using saliva as the liquid excreted from the body.

Figure 1B:
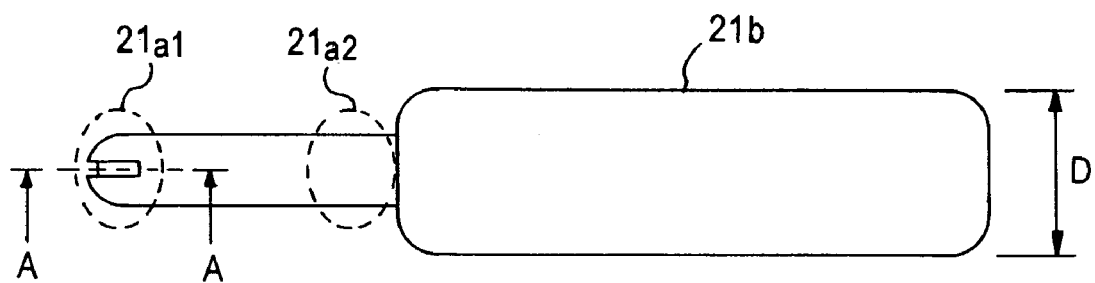
Figure 1C:
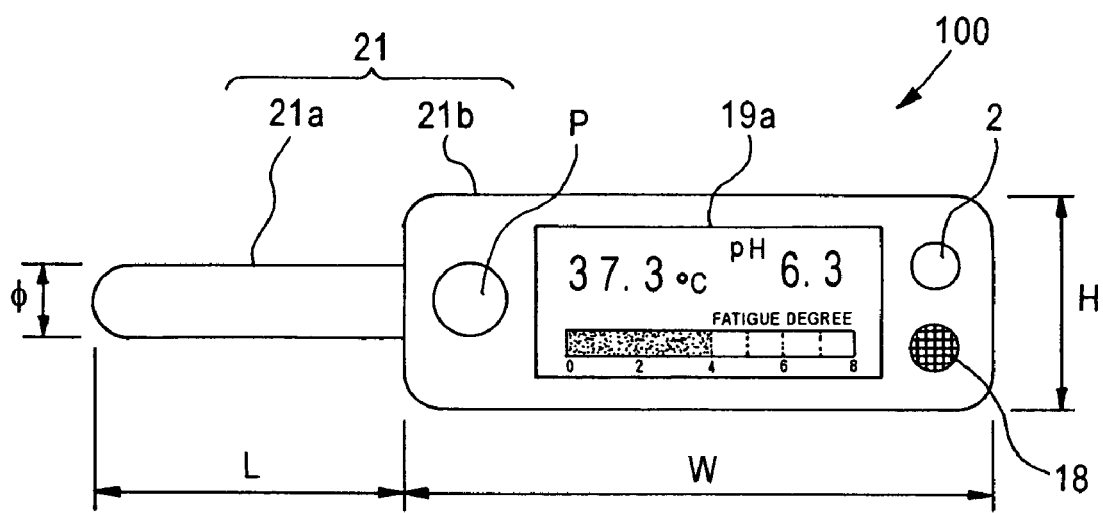
Figure 2:
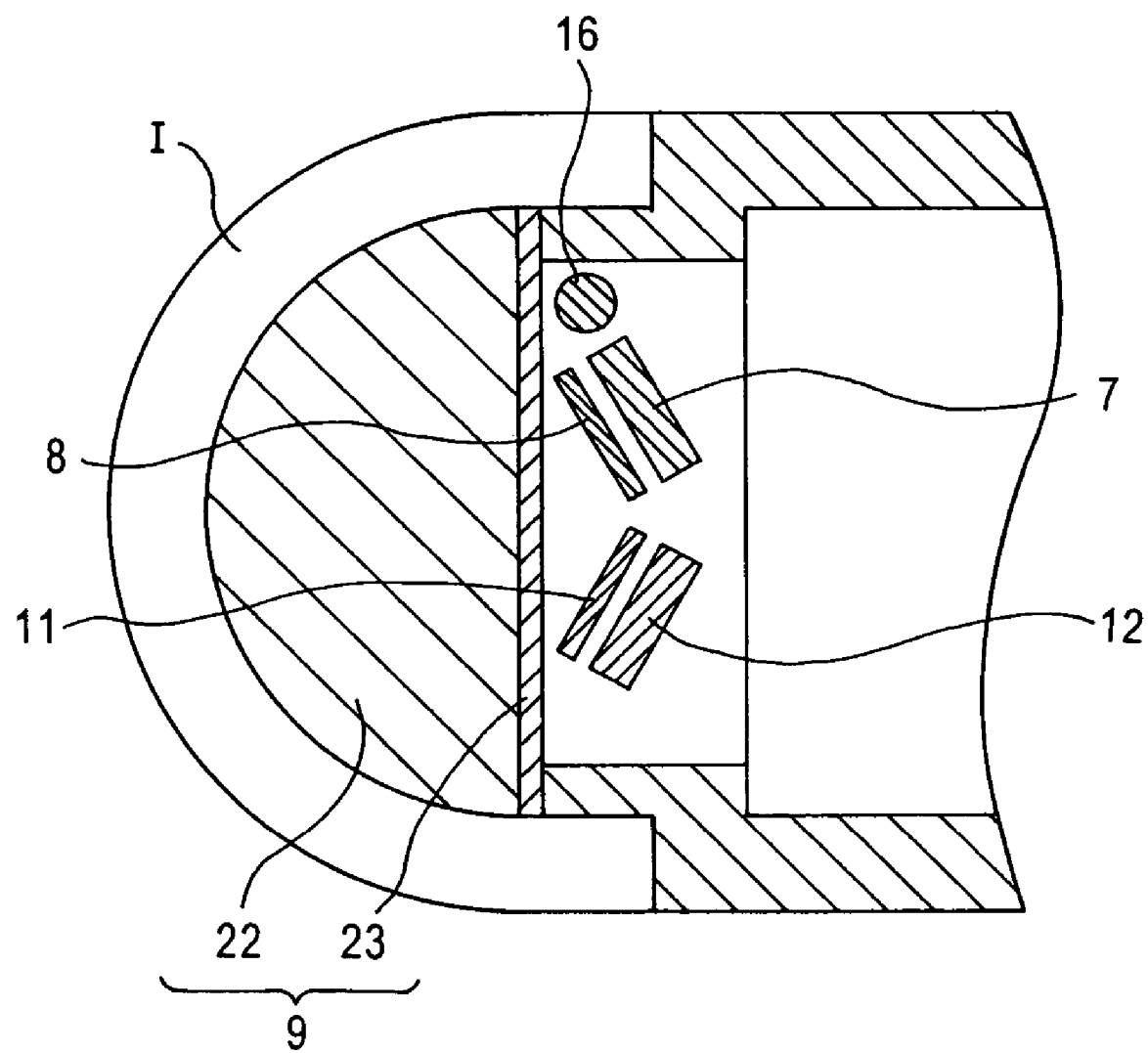
FIG. 2 is a partial sectional view taken through line A-A of FIG. 1B.
Figure 3:
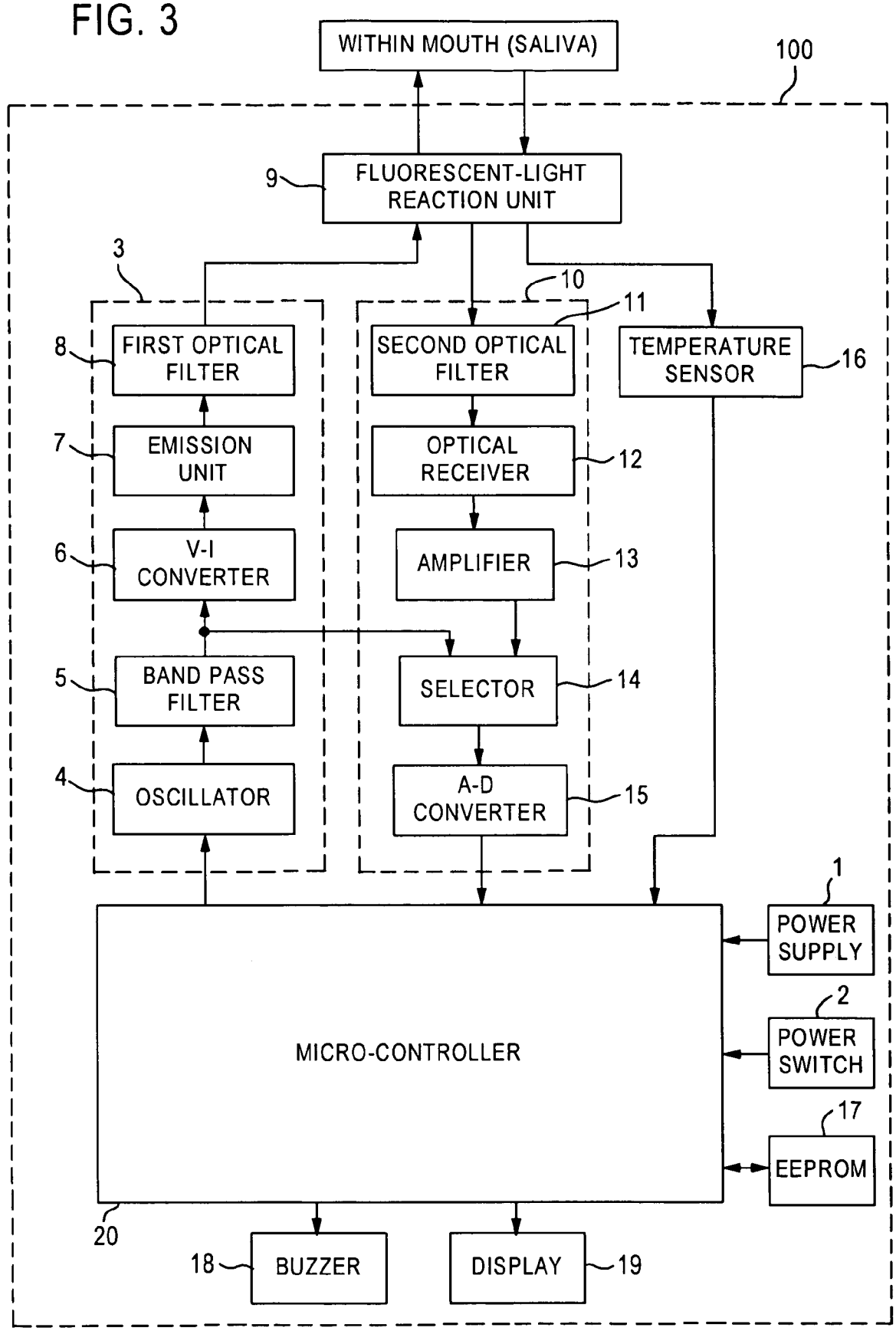
FIG. 3 is a block diagram of a fatigue-degree evaluation device according to an embodiment of the present invention.

First, with reference to the exterior views of FIGS. 1A to 1C, the partial sectional view of FIG. 2, the block diagram of FIG. 3, the display screen drawing of FIG. 4, and the evaluation reference (the relationship table between the pH of saliva and the fatigue degree) of FIG. 5, the structure of a fatigue degree evaluation device according to an embodiment of the present invention will be described in detail.

A fatigue degree evaluation device 100 includes a power supply 1, a power switch 2, a radiating unit 3 (comprising an oscillator 4, a BPF (band pass filter) 5, a V-I converter 6, an emission unit 7, and a first optical filter 8), a fluorescent-light reaction unit 9, a detecting unit 10 (comprising a second optical filter 11, an optical receiver 12, an amplifier 13, a selector 14, and an A-D converter 15), a temperature sensor 16, an EEPROM (electrically erasable programmable read only memory) 17, a buzzer 18, a display 19 and a micro-controller 20, which are arranged within a casing 21.

The casing 21 is composed of a bar-like body 21a and a holding body 21b. The bar-like body 21a is formed of a bar (length L: 50 mm or less, diameter φ: about 10 mm) having an extremity $21a_1$ with a bifurcated end and a connection part $21a_2$, and is provided with a lead-in path 1 arranged at the extremity $21a_1$ for leading saliva to the fluorescent-light reaction unit 9. The holding body 21b is made to be easily held by a user's hand at the connection part $21a_2$. More specifically, the holding body 21b has front and back surfaces (width W and height H: 20 mm or more) and top and bottom surfaces (width W and depth D), which extend in the longitudinal direction of the bar-like body 21a. The width W of the front and back surfaces is larger than the height H; the depth D of the top and bottom surfaces is smaller than the height H of the front and back surfaces. The front and back surfaces are provided with a recess P.

The power supply 1 is within the holding body 21b for supplying electric power to each point of an electric system.

The power switch 2 is in the front of the holding body 21b for switching on/off the power supply from the power supply 1 to each point of the electric system.

The radiating unit 3 includes the oscillator 4, the BPF 5, the V-I converter 6, and the first optical filter 8, and it radiates reference light based on an AC constant current. The oscillator 4 herein generates an AC constant voltage by the control of the micro-controller 20. The BPF 5 smoothes the waveform of the AC constant voltage generated by the oscillator 4 so as to be entered in the V-I converter 6 and the selector 14. The V-I converter 6 converts the AC constant voltage passed through the BPF 5 into the AC constant current (1 KHz, preferably) so as to be outputted. The emission unit 7 (a light emitting diode (LED), for example) generates reference light to be used by the fluorescent-light reaction unit 9 based on the AC constant current from the V-I converter 6. The first optical filter 8 (a lens, for example) diffuses the reference light from the emission unit 7 to the fluorescent-light reaction unit 9.

The fluorescent-light reaction unit 9 comprises a liquid-adsorption member 22 and a fluorescent screen 23, and it retains saliva thereon, and absorbs the reference light diffused by the first optical filter 8 so as to generate fluorescent light by the excitation due to this absorption.

The liquid-adsorption member 22 herein is made of a material adsorbing and retaining saliva such as a sponge. The fluorescent screen 23 is arranged in contact with the liquid-adsorption member 22 and made of a transparent material, such as a plastic, having a fluorescent substance adhered on the contact surface.

The detecting unit 10 is composed of the second optical filter 11, the optical receiver 12, the amplifier 13, the selector 14, and the A-D converter 15, and it detects fluorescent light generated by the fluorescent-light reaction due to the fluorescent-light reaction unit 9. The second optical filter 11, such as a lens, condenses the fluorescent light generated in the fluorescent screen 23. The optical receiver 12, such as a photo-diode (PD), receives the fluorescent light from the second optical filter 11 so as to produce a voltage due to the received light. The amplifier 13 amplifies the voltage from the optical receiver 12 so as to be entered in the selector 14. The selector 14 switches the connection to one of the BPF 5 and the amplifier 13 based on the control from the micro-controller 20. The A-D converter 15 converts the analog voltage from the selector 14 into the digital voltage so as to be entered in the micro-controller 20.

The temperature sensor 16 is arranged in close vicinity to the fluorescent-light reaction unit 9, and it detects the temperature of saliva with a voltage so as to be entered in the micro-controller 20. According to this embodiment of the present invention, saliva within the oral cavity is measured, and the saliva temperature is assumed to be at the body temperature.

The EEPROM 17 stores the evaluation about the fatigue degree as temporal data based on the control of the micro-controller 20.

The buzzer 18 is arranged in the front of the holding body 21b, and it generates intermittent sounds for informing the user that the fluorescent light or the temperature of saliva is not normal or that the elapsed time of the measurement exceeds one minute, and it also generates a continuous sound for informing the user of the completion of measurement, based on the control of the micro-controller 20.

Figures 4, 5:
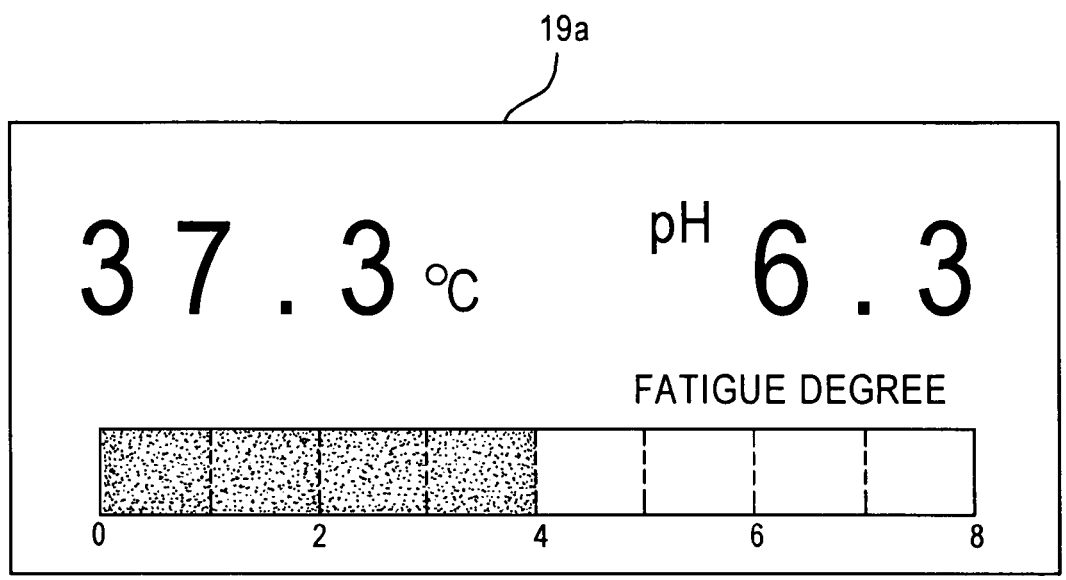
FIG. 4 is a view of a screen of a display of a device according to an embodiment of the present invention.
FIG. 5 is an evaluation reference table showing the correspondence between saliva pH and fatigue degree.

The display 19 is arranged in the front of the holding body 21b, and as shown in FIG. 4 in detail, it displays the evaluation result of the body temperature numerically on the upper left of a screen 19a and the evaluation result of the saliva pH numerically on the upper right, and the display 19 also displays the evaluation result of the fatigue degree with a horizontal bar chart on the lower portion, based on the control of the micro-controller 20. When the device is not in a state wherein the temperature has been normally measured, "-" is displayed, which means an abnormal state.

The micro-controller 20 includes a CPU, an ROM, an RAM, a timer, and an IO port for performing the following operations:

i) The micro-controller 20 switches the connection of the selector 14 to one of the BPF 5 and the amplifier 13; when connected to the BPF 5, the output from the A-D converter 15 is voltage representative of the reference light to be radiated on the saliva (hereinafter "reference light voltage"); and when connected to the amplifier 13, the output from the A-D converter 15 is voltage due to the fluorescent light of the saliva (hereinafter "fluorescent light voltage")

ii) The voltage detected by the temperature sensor 16 is substituted into the following equation (1) below to calculate the saliva temperature (body temperature) as well as control the display 19 to display the calculated result;

iii) The reference light voltage, the fluorescent light voltage, and the temperature of the saliva are substituted into equation (2) below to calculate the saliva pH as well as display the calculated result on the display 19;

iv) The saliva pH is evaluated regarding the fatigue degree based on the evaluation reference table shown in FIG. 5 to display the evaluation result on the display 19;

v) The fluorescent light voltage from the A-D converter 15 and the reference light voltage are substituted into equation (3) below to obtain the ratio between the fluorescent light voltage and the reference light voltage, and to determine whether the fluorescent light generated via saliva has been normally measured based on the determination references of equations (4) and (5) below (if both the determination references are satisfied, it is determined normal, and if one or the other of them is not satisfied, it is determined abnormal); when the fluorescent light generated via the saliva is determined normal, the result is incorporated as fluorescent data, and if the fluorescent light is determined abnormal, the buzzer 18 is controlled to generate intermittent sounds;

vi) Based on the determination reference that the measurement is normal if the previously calculated saliva temperature (body temperature) is higher than 35° C. (abnormal when it is less than 35° C.), the saliva temperature is determined to be measured normally or not; when being determined normal, the result is incorporated as temperature data, and when being not determined normal, the display 19 is controlled to display "-";

vii) The elapsed time of measurement is determined to be more than one minute or not, and when it is determined to exceed one minute, the buzzer 18 is controlled to generate intermittent sounds, and when the elapsed time does not exceed one minute, the selector 14 is controlled to switch to the BPF 5.

$$T = \alpha \times Vt + \beta \quad (1)$$

$$pH = p \times \arg[\{(a \times T + b) \times \text{Vhum} + c\}/\{(d \times T + e) \times \text{Vref})\} + \delta] + q \quad (2)$$

$$D = \text{Vhum}/\text{Vref} \quad (3)$$

$$|D| > D\text{th} \quad (4)$$

$$\theta \min < \arg(D) < \theta \max \quad (5),$$

where

T: saliva temperature (body temperature),

Vt: voltage based on the saliva temperature (body temperature),

D: ratio between fluorescent light (voltage) and reference light (voltage),

Vref: reference light (voltage) to be radiated on saliva,

Vhum: fluorescent light (voltage) of saliva, pH: pH of saliva,

Dth: threshold value showing the signal intensity for obtaining a normal result (constant obtained in advance by experiments), θ: phase of fluorescent light (voltage) relative to the reference light (voltage) (constant obtained in advance by experiments), and α, β, δ, a, b, c, d, e, p, q: constant (constants obtained in advance by experiments).

The structure comprising the radiating unit 3, the fluorescent-light reaction unit 9, the detecting unit 10, the micro-controller 20, and the power supply 1 corresponds to a fluorescent light measuring means. The structure composed of the temperature sensor 16, the micro-controller 20, and the power supply 1 corresponds to a temperature measuring means. Further, the structure composed of the buzzer 18, the micro-controller 20, and the power supply 1 corresponds to a fluorescent-light measurement determination processing means, a temperature measurement determination processing means, and an elapsed time measurement determination processing means. Furthermore, the structure composed of the micro-controller 20 and the power supply 1 corresponds to a clock means, a pH calculating means, and a fatigue degree evaluating means.

Figure 6:
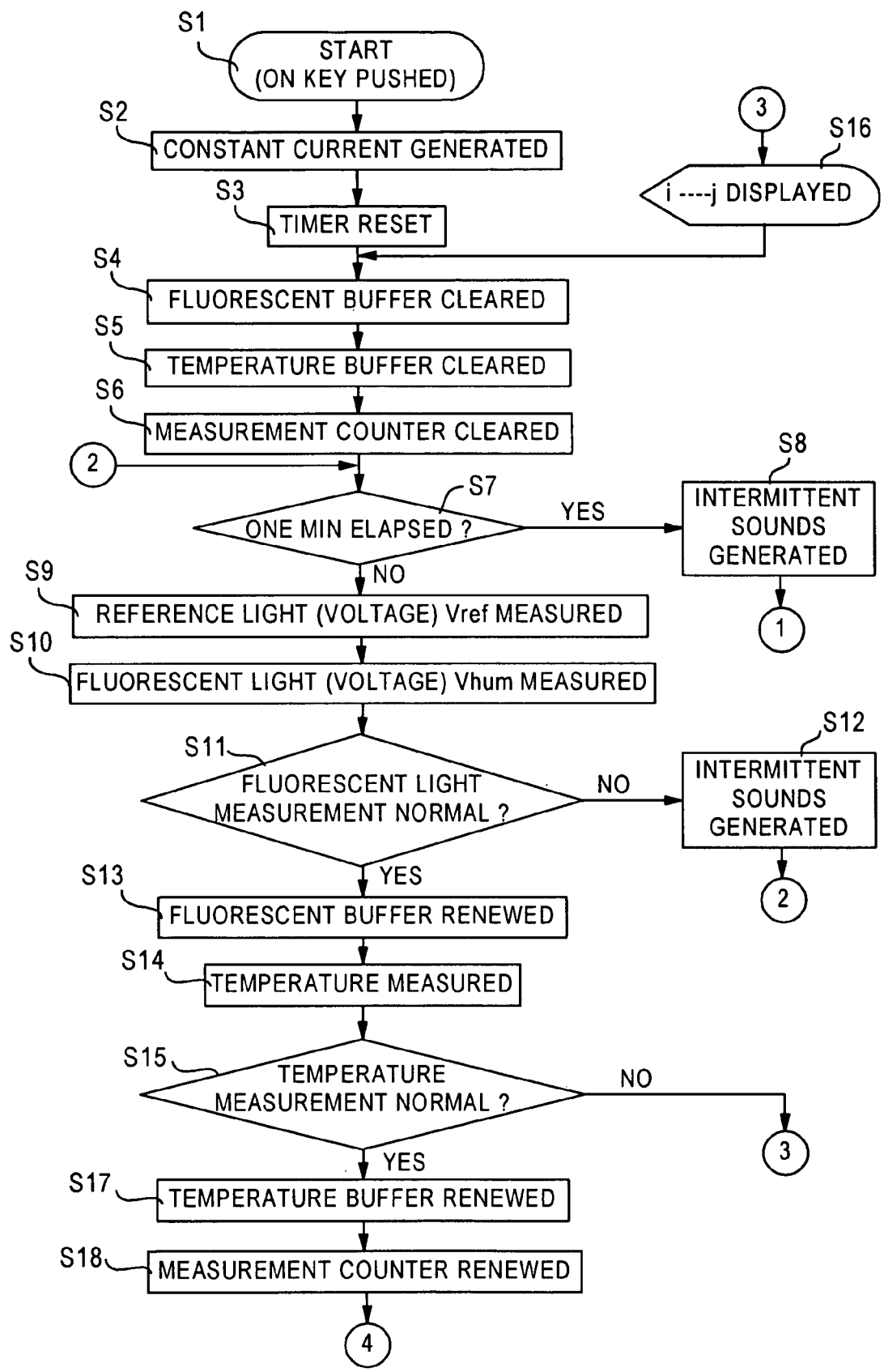
FIG. 6 is a flowchart of the flow of the operation and processing of a fatigue-degree evaluation device according to an embodiment of the present invention.
Figure 6:
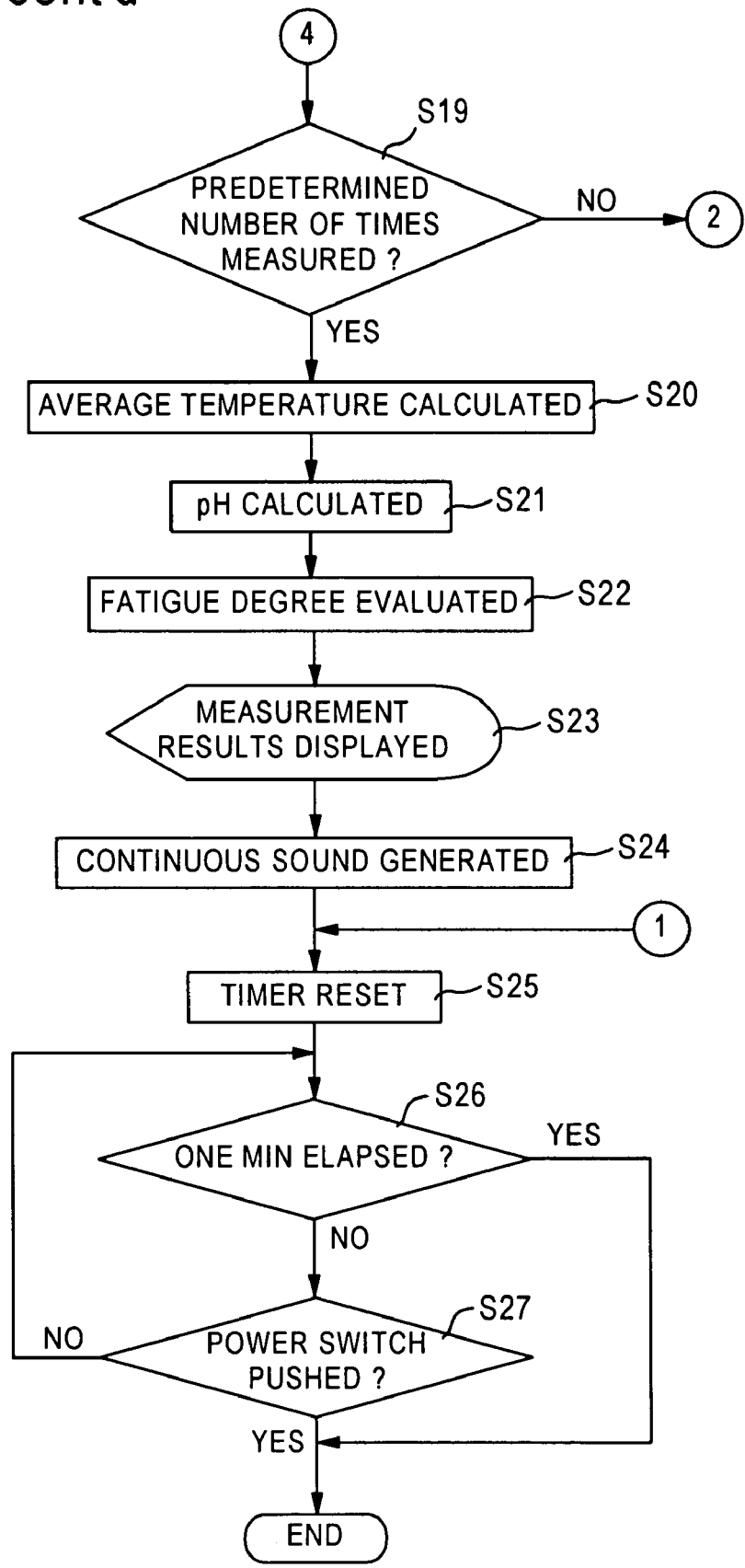

Next, with reference to the flowchart of FIG. 6, the operation of the above described fatigue degree evaluation device according to an embodiment of the present invention will be described.

First, when the power switch 2 is pushed on, electric power is supplied from the power supply 1 to each point of the electric system (Step S1), and the reference light based on the AC constant current (1 kHz) produced through the oscillator 4, the BPF 5, and the V-I converter 6 is generated (diffused) from the first optical filter 8 to the fluorescent-light reaction unit 9 (Step S2).

Then, the timer is reset in the micro-controller 20 (Step S3); the fluorescent light buffer is cleared (Step S4); the temperature buffer is cleared (Step S5); and the measurement counter is cleared (Step S6).

Continuously, in the micro-controller 20, the elapsed time of measurement is determined whether it exceeds one minute or not (Step S7). When it exceeds one minute (YES at Step S7), the buzzer 18 generates intermittent sounds (Step S8) based on the output control by the micro-controller 20 so as to proceed to the below-mentioned processing at Step S25. On the other hand, when the elapsed time does not exceed one minute (NO at Step S7), the selector 14 switches the connection to the BPF 5 based on the control of the micro-controller 20 so as to measure the reference light voltage (Step S9).

Thereafter, the selector 14 switches the connection to the amplifier 13 based on the control of the micro-controller 20 so as to measure the fluorescent light voltage (Step S10).

Then, in the micro-controller 20, the measured fluorescent light voltage and the reference light voltage are substituted into the equation (3) so as to obtain the ratio between the fluorescent light voltage and the reference light voltage, so that the measurement of the fluorescent light generated via the saliva is determined to be normal or not (Step S11) based on the determination references of the equations (4) and (5). When the measurement is not normal (NO at Step S11), the buzzer 18 generates intermittent sounds (Step S12) based on the control by the micro-controller 20 so as to return to the processing at Step S7. On the other hand, when the measurement is normal (YES at Step S11), the fluorescent light voltage in the fluorescent light buffer is accumulatively renewed (Step S13).

Continuously, the connection is switched to the temperature sensor 16 based on the control of the micro-controller 20 so as to measure the voltage based on the saliva temperature (body temperature) and calculate the saliva temperature (body temperature) (Step S14) by substituting the voltage into the equation (1). On the basis of the determination reference that measurement is normal when the saliva temperature (body temperature) is higher than 35° C., the measurement of the saliva temperature is determined to be normal or not (Step S15). If the measurement is not normal as a result of the determination (NO at Step S15), the display 19 displays "–" (Step S16) so as to return to the processing at Step S4. On the other hand, when the measurement is normal as a result of the determination (YES at Step S15), the voltage based on the saliva temperature in the temperature buffer is accumulatively renewed (Step S17).

In succession, in the micro-controller 20, by adding one to the present value of the measurement counter, the value of the measurement counter is accumulatively renewed (Step S18).

Then, in the micro-controller 20, the renewed value of the measurement counter is determined to be a predetermined number of times (10) or not (Step S19). The reason why the predetermined number of times is ten is that the number is the minimal measurement time to secure estimated accuracies and suitable for measuring the fluorescent light generated via the saliva and the temperature (body temperature) of the saliva.

If the value of the measurement counter has not reached the predetermined number (10) as a result of the determination (NO at Step S19), the process proceeds to the processing at Step S7. On the other hand, when the value reaches the predetermined number (10) as a result of the determination (YES at Step S19), in the micro-controller 20, by dividing the voltage based on the saliva temperature (body temperature) accumulatively renewed in the temperature buffer by the predetermined number (10) of the measurement counter, the average of the sampled saliva temperatures (body temperatures) is calculated. By substituting the voltage based on the average saliva temperature (body temperature) into equation (1), the saliva temperature (body temperature) is calculated (Step S20).

Then, in the micro-controller 20, the fluorescent light voltage accumulatively renewed in the fluorescent light buffer is divided by the predetermined number (10) of the measurement counter so as to calculate the average of the sampled fluorescent light voltage. By substituting the average fluorescent light voltage and the previously calculated saliva temperature (body temperature) into equation (2), the saliva pH is calculated (Step S21).

Continuously, in the micro-controller 20, with reference to the evaluation reference shown in FIG. 5, the fatigue degree corresponding to the calculated saliva pH is evaluated (Step S22). More specifically, when the calculated saliva pH is 6.0, the fatigue degree is numerically evaluated as 1.0.

Then, as shown in FIG. 4, the evaluation of the fatigue degree, the saliva pH, and the saliva temperature (body temperature) are displayed on the display 19 as measured results (Step S23) based on the control of the micro-controller 20 so as to allow the buzzer 18 to generate intermittent sounds informing measurement completion for a predetermined period of time (3 seconds) (Step S24).

Continuously, in the micro-controller 20, the timer is reset (Step S25), and the elapsed time of measurement is determined to have exceeded one minute or not (Step S26). When the elapsed time exceeds one minute as a result of this determination (YES at Step S26), the electric power supply from the power supply 1 to each point of the electric system is stopped so as to complete a series of the processing based on the control of the micro-controller 20. On the other hand, if the elapsed time does not exceed one minute as a result of the determination (NO at Step S26), it is determined whether the power switch 2 is pushed on or not (Step S27).

Then, in the micro-controller 20, when the power switch 2 is not pushed (NO at Step S27), the process proceeds to the processing at Step S26. On the other hand, when the power switch 2 is pushed (YES at Step S27), the electric power supply from the power supply 1 to each point of the electric system is stopped so as to complete a series of the processing based on the control of the micro-controller 20.

The above description relates to a fatigue-degree evaluation device according to the present invention wherein the liquid excreted from the body is human saliva.

According to another embodiment of the present invention by substituting an evaluation reference showing correspondence between urine pH and the fatigue degree for the evaluation reference in FIG. 5 showing correspondence between saliva pH and the fatigue degree, the inventive device can be operable by measuring human urine. In this case, the measurement is performed by directly pouring urine on the bar-like body 21a, or by immersing part of the bar-like body 21a in a urine contained in a container.

According to the embodiments described above, the measurement is for human beings; however, by substituting an evaluation reference for animals other than humans for the evaluation reference for humans shown in FIG. 5, the inventive device can be operable by measuring saliva or urine of animals other than humans.

According to the embodiment described above, there is provided a temperature sensor 16 so that the saliva pH is calculated in view of the saliva temperature (body temperature); alternatively, the inventive device may also be operable without the temperature sensor 16. In this case, the saliva pH may be calculated according to the following equation (6):

$$pH = p \times \arg[(\gamma \times Vhum + \epsilon)/(\phi \times Vref) + \delta)] + q \quad (6),$$

where pH: pH of the liquid excreted from the body,

Vhum: the fluorescent light voltage of the liquid excreted from the body,

Vref: the reference light voltage, with which the liquid excreted from the body is irradiated, and p, q, δ, ε, 100 , δ: constant.

Figure 7:
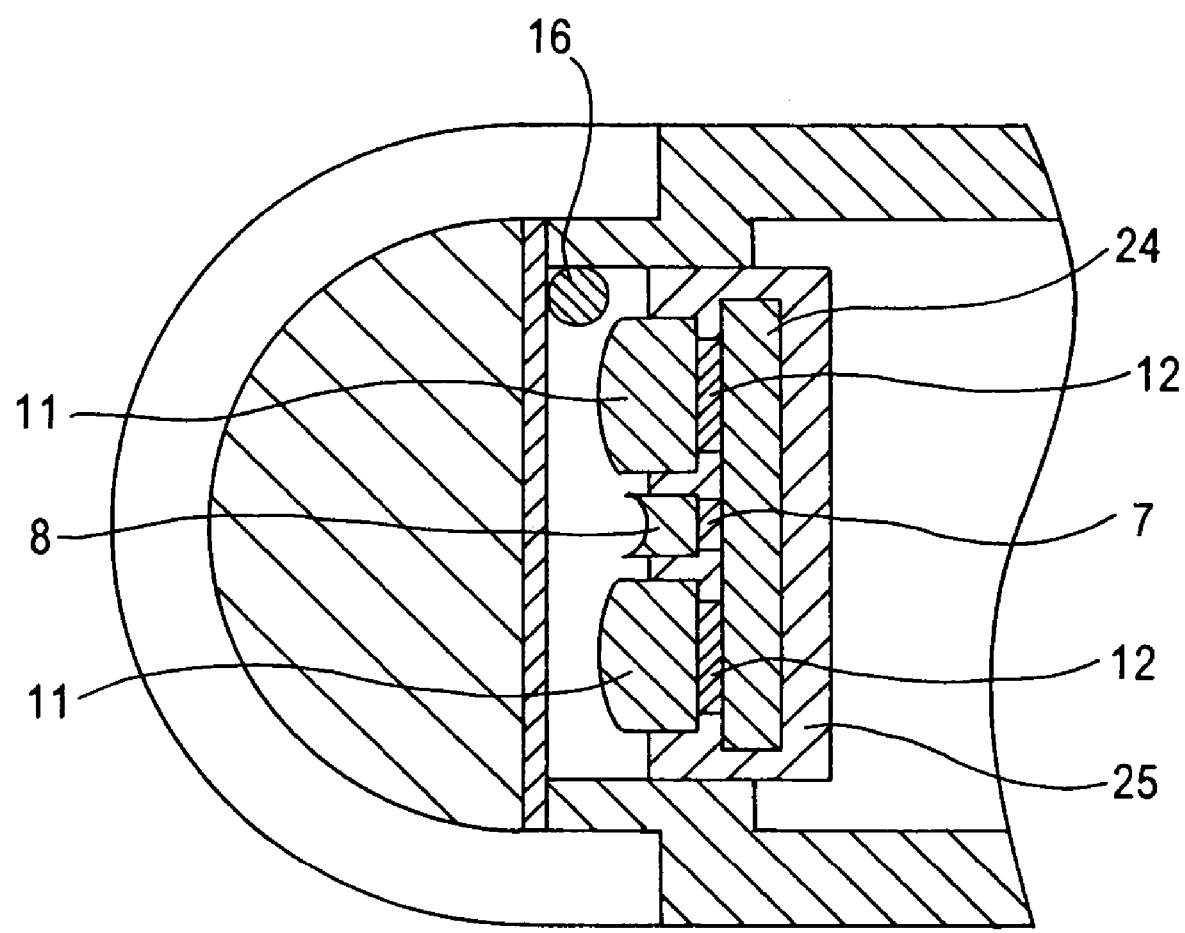
FIG. 7 is another partial sectional view taken through line A-A of FIG. 1B.

According to the embodiment described above, the emission unit 7, the first optical filter 8, the second optical filter 11, and the optical receiver 12 are individually arranged within the bar-like body 21a; alternatively, as shown in the partial sectional view of FIG. 7, the emission unit 7 (LED) and the first optical filter 8 (concave lens) may be arranged in the center of a substrate 24, and the second optical filter 11 (convex lens) and the optical receiver 12 may be arranged on peripheries of the emission unit 7 and the first optical filter 8, so as to be arranged within the bar-like body 21a in a state that they are packaged integrally in a package 25 as an optical system unit.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processes and structures have not been described in detail, in order not to unnecessarily obscure the present invention.

Only selected embodiments of the present invention and a few examples of its versatility are shown and described in the present disclosure. It is to be understood that the invention is capable of use in various other combinations and environments and is capable of changes or modifications within the scope of the inventive concept as expressed herein.

What is claimed is:

1. A fatigue-degree evaluation device comprising:
   a fluorescent-light reaction unit for retaining a liquid excreted from the body thereon and for fluorescent-reacting using the liquid and a reference light;
   a detection unit for detecting fluorescent light generated based on the fluorescent reaction of the fluorescent-light reaction unit; and
   a processor for measuring the detected fluorescent light, calculating a pH based on the measurement of the fluorescent light, and evaluating a fatigue degree based on the pH.

2. The device according to claim 1, wherein the processor is further configured to:
   determine whether the measurement of the fluorescent light is normal;
   store the measurement result as fluorescent light data when the fluorescent light is determined to have been measured normally, and
   inform a user when the fluorescent light is determined to have not been measured normally.

3. The device according to claim 1, further comprising a temperature sensor for detecting the temperature of the liquid excreted from the body,
   wherein the processor calculates the pH based on the fluorescent light and the temperature of the liquid.

4. The device according to claim 2, further comprising a temperature sensor for detecting the temperature of the liquid excreted from the body,
   wherein the processor calculates the pH based on the fluorescent light and the temperature of the liquid.

5. The device according to claim 3, wherein the processor is further configured to:
   determine whether the whether the measurement of the temperature is normal;
   store the measurement result as temperature data when the temperature is determined to have been measured normally, and inform a user when the temperature is determined to have not been measured normally.

6. The device according to claim 4, wherein the processor is further configured to:
   determine whether the measurement of the temperature is normal;
   store the measurement result as temperature data when the temperature is determined to have been measured normally, and
   inform a user when the temperature is determined to have not been measured normally.

7. The device according to claim 2, wherein the processor is further configured to:
   measure an elapsed time of measurement;
   determine whether the elapsed time of measurement measured exceeds a predetermined time;
   inform the user when the elapsed time exceeds the predetermined time; and
   control the fluorescent-light reaction unit, detection unit and processor to measure the fluorescent light when the elapsed time does not exceed the predetermined time.

8. The device according to claim 5, wherein the processor is further configured to:
   measure an elapsed time of measurement;
   determine whether the elapsed time of measurement exceeds a predetermined time;
   inform the user when the elapsed time exceeds the predetermined time; and
   control the fluorescent-light reaction unit, detection unit and processor to measure the fluorescent light when the elapsed time does not exceed the predetermined time.

9. The device according to claim 6, wherein the processor is further configured to:
   measure an elapsed time of measurement;
   determine whether the elapsed time of measurement exceeds a predetermined time;
   inform the user when the elapsed time exceeds the predetermined time; and
   control the fluorescent-light reaction unit, detection unit and processor to measure the fluorescent light when the elapsed time does not exceed the predetermined time.

10. The device according to claim 1, comprising a radiating unit for radiating the reference light based on an AC constant current.

11. The device according to claim 10, wherein the radiating unit, the fluorescent-light reaction unit, the detection unit and the processor comprise a bar-like body, comprising a bar having an extremity with a bifurcated end and a connection part, and having a lead-in path arranged at the extremity for leading the liquid excreted from the body to the fluorescent-light reaction unit, and a holding body made to be easily held by a hand at the connection part, so as to form a casing.

12. The device according to claim 11, wherein the holding body is formed of front and back surfaces, having a width and a height, and top and bottom surfaces, having a width and a depth; the holding body extending in the longitudinal direction of the bar-like body, the width of the front and back surfaces being larger than their height, the depth of the top and bottom surfaces being smaller than the height of the front and back surfaces, and a recess being provided in the front and back surfaces.

13. The device according to claim 12, wherein the height of the front and back surfaces is not less than 20 mm.

14. The device according to claim 11, wherein the bar-like body does not exceed 50 mm in length.

15. The device according to claim 10, wherein the fluorescent-light reaction unit comprises a liquid-adsorption member, and a fluorescent screen in contact with the liquid-adsorption member and having a fluorescent substance adhered thereon,
   wherein the radiating unit comprises an emission unit for radiating the reference light and a first optical filter for diffusing the reference light from the emission unit to the fluorescent screen, and
   wherein the detection unit comprises a second optical filter for condensing the fluorescent light generated in the fluorescent screen and an optical receiver for receiving the fluorescent light from the second optical filter.

16. The device according to claim 15, wherein the emission unit, the first optical filter, the second optical filter, and the optical receiver constitute a packaged optical system unit.

17. The device according to claim 1, wherein the liquid excreted from the body is saliva.

18. The device according to claim 1, wherein the liquid excreted from the body is urine.

19. A fatigue-degree evaluation device comprising:
   fluorescent-light measuring means for measuring the fluorescent light generated via a liquid excreted from a body;
   pH calculating means for calculating a pH based on the fluorescent light, measured by the fluorescent-light measuring means, generated via the liquid excreted from the body; and
   fatigue-degree evaluating means for evaluating a fatigue degree based on the pH calculated by the pH calculating means.

20. The device according to claim 19, further comprising fluorescent-light measurement determination processing means for determining whether the fluorescent-light measuring means has normally measured the fluorescent light of the liquid excreted from the body,
   wherein when the fluorescent light of the liquid excreted from the body is determined to have been normally measured, the result is incorporated as fluorescent light data, and when the fluorescent light of the liquid excreted from the body is determined to have not been normally measured, a user is so informed.

21. The device according to claim 19, further comprising temperature measuring means for measuring the temperature of the liquid excreted from the body,
   wherein the pH calculating means calculates the pH based on the fluorescent light, measured by the fluorescent-light measuring means, generated via the liquid excreted from the body and the temperature, measured by the temperature measuring means, of the liquid excreted from the body.

22. The device according to claim 21, further comprising temperature measurement determination processing means for determining whether the temperature measuring means has normally measured the temperature of the liquid excreted from the body,
   wherein when the temperature of the liquid excreted from the body is determined to have been normally measured, the result is incorporated as temperature data, and when the temperature of the liquid excreted from the body is determined to have not been normally measured, a user is informed of the result.

23. The device according to claim 20, further comprising:

clock means for measuring an elapsed time of measurement; and elapsed-time measurement determination processing means for determining whether the elapsed time of measurement measured by the clock means exceeds a predetermined time, wherein when the elapsed time exceeds the predetermined time, a user is informed, and when the elapsed time does not exceed the predetermined time, the fluorescent-light measuring means is controlled to measure the fluorescent light.

* * * * *